(12) United States Patent
Li et al.

(10) Patent No.: US 8,431,371 B2
(45) Date of Patent: *Apr. 30, 2013

(54) EXPRESSION SYSTEM FOR PRODUCING MULTI-ENZYME COMPLEXES AND USES THEREOF

(75) Inventors: Wen-Hsiung Li, Taipei (TW);
Ming-Che Shih, Taipei (TW);
Chieh-Chen Huang, Taichung (TW);
Jui-Jen Chang, Kaohsiung (TW);
Cheng-Yu Ho, Bade (TW)

(73) Assignee: Academia Sinica, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/306,056

(22) Filed: Nov. 29, 2011

(65) Prior Publication Data

US 2012/0083012 A1 Apr. 5, 2012

Related U.S. Application Data

(63) Continuation-in-part of application No. 12/621,805, filed on Nov. 19, 2009.

(51) Int. Cl.
*C12P 7/16* (2006.01)
*C12P 7/10* (2006.01)
*C12P 7/06* (2006.01)

(52) U.S. Cl.
USPC ........ 435/135; 435/160; 435/161; 435/252.3; 435/320.1; 435/289.1; 536/23.2

(58) Field of Classification Search .................. None
See application file for complete search history.

(56) References Cited

U.S. PATENT DOCUMENTS

| | | | | |
|---|---|---|---|---|
| 6,365,390 | B1 * | 4/2002 | Blum et al. | 435/197 |
| 6,602,700 | B1 * | 8/2003 | Li et al. | 435/267 |
| 7,977,076 | B2 * | 7/2011 | Oyler | 435/135 |
| 8,334,121 | B2 * | 12/2012 | Schindler et al. | 435/160 |
| 2003/0027298 | A1 * | 2/2003 | Bott et al. | 435/183 |
| 2006/0105442 | A1 * | 5/2006 | Wu et al. | 435/161 |
| 2006/0105914 | A1 * | 5/2006 | Taylor et al. | 504/117 |
| 2009/0035811 | A1 * | 2/2009 | Kohda et al. | 435/41 |
| 2009/0077863 | A1 * | 3/2009 | Oyler | 44/307 |
| 2010/0304405 | A1 * | 12/2010 | Fox et al. | 435/7.4 |
| 2011/0008489 | A1 * | 1/2011 | Robb et al. | 426/18 |
| 2011/0076733 | A1 * | 3/2011 | Urano et al. | 435/160 |
| 2011/0097769 | A1 * | 4/2011 | Del Cardayre et al. | 435/134 |

(Continued)

FOREIGN PATENT DOCUMENTS

WO 2008/100251 * 8/2008

OTHER PUBLICATIONS

Han et al, 2003, Journal of Bacteriology, vol. 185(6) pp. 2520-2527, Transcription of *Clostridium cellulovorans* cellulosomal celulase and hemicellulase genes.*

(Continued)

*Primary Examiner* — Albert Navarro
*Assistant Examiner* — Ginny Portner
(74) *Attorney, Agent, or Firm* — Occhiuti Rohlicek & Tsao LLP (57) ABSTRACT

An expression system for producing a multi-enzyme complex, the system including a nucleic acid molecule containing a promoter operatively linked to a nucleotide sequence including multiple genes encoding multiple enzymes that are components of the multi-enzyme complex.

12 Claims, 10 Drawing Sheets

U.S. PATENT DOCUMENTS

| | | | |
|---|---|---|---|
| 2011/0129876 A1* | 6/2011 | Fierobe et al. | 435/69.52 |
| 2011/0236943 A1* | 9/2011 | Girbal et al. | 435/161 |
| 2011/0294184 A1* | 12/2011 | Fierobe et al. | 435/170 |
| 2011/0306105 A1* | 12/2011 | Chen et al. | 435/165 |

OTHER PUBLICATIONS

Hoffmann, Frank et al, FEMS Microbiology Letters, vol. 177, 1999, pp. 327-334, Heat inactivation of plasmid encoded C857 repressor induced gene expression from Ind- lambda prophage in recombinant *Escherichia coli.*\*

Mitsuzawa, S et al, Journal of Biotechnology, vol. 143, pp. 139-144, 2009, The rosettazyme, A synthetic cellulosome.*

Johnson et al., "Saccharification of Complex Cellulosic Substrates by the Cellulase System from *Clostridium thermocellum*," Applied and Environmental Microbiology, 43(5):1125-1132 (1982).

Schwarz, W.H., "The cellulosome and cellulose degradation by anaerobic bacteria," App. Microbiol. Biotechnol. 56:634-649 (2001).

Mingardon et al., "Exploration of New Geometries in Cellulosome-Like Chimeras," Applied and Environmental Microbiology, 73(22):7138-7149 (2007).

Murashima et al., "Heterologous Production of *Clostridium cellulovorans engB*, Using Protease-Deficient *Bacillus subtilis*, and Preparation of Actove Recombinant Cellulosomes," Journal of Bacteriology, 184(1):76-81 (2002).

Nishizaki et al., "Metabolic Engineering of Carotenoid Biosynthesis in *Escherichia coli* by Ordered Gene Assembly in *Bacillys subtilis*," Applied and Environmental Microbiology, 73(4):1355-1361 (2007).

Wilson, David B., "Cellulases and biofuels," Current Opinion in Biotechnology, 20:295-299 (2009).

Tsunge et al., "One Step Assembly of Multiple DNA Fragments with a Designed Order and Orientation in *Bacillus subtilis* Plasmid," Nucleic Acids Research, 31(2I):1-8 (2003).

Bayer et al., "The Potential of Cellulases and Cellulosomes for Cellulosic Waste Management," Current Opinion in Biotechnology, 18:237-245 (2007).

Bayer at al., "Cellulosomes—Structure and Ultrastructure," Journal of Structural Biology, 124:221-234 (1998).

Gold, Nicholas D. and Vincent J.J. Martin, "Global View of *Clostridium thermocellum* Cellulosome Revealed by Quantitative Proteomic Analysis," Journal of Bacteriology, 189(19):6787-6795 (2007).

\* cited by examiner

EXPRESSION SYSTEM FOR PRODUCING MULTI-ENZYME COMPLEXES AND USES THEREOF

CROSS REFERENCE TO RELATED APPLICATION

This application is a continuation-in-part of U.S. patent application Ser. No. 12/621,805, filed Nov. 19, 2009, the content of which is incorporated herein by reference in its entirety.

BACKGROUND OF THE INVENTION

Multi-enzyme complexes increase the rate and efficiency of the reactions catalyzed by enzymes. Such multi-enzyme complexes have numerous industrial applications. For example, lignocellulosic biomass, rich in cellulose and hemicellulose, has become of particular interest due to its potential use in biofuel production. More specifically, the cellulose and hemicellulose can be hydrolyzed to produce fermentable sugars, which are precursors to ethanol and other biofuels.

One barrier to preparation of biofuels from lignocellulosic biomass is that the fermentable sugars are trapped inside the lignocellulose. Multiple enzymes (e.g., endoglucanase, beta-glucosidase, and cellubiohydrolase) are needed to produce fermentable sugars from cellulose released from biomass via delignification.

There is a need to develop high order multi-enzyme complexes for use in efficient degradation of biomass and other purposes.

SUMMARY OF THE INVENTION

In one aspect, described herein is an expression system that includes a nucleic acid molecule containing a promoter (e.g., a thermo-inducible promoter) operatively linked to a nucleotide sequence (e.g., a polycistronic nucleotide sequence) including 1-150 genes encoding enzymes that are components of a multi-enzyme complex. The genes of the nucleotide sequence are regulated artificially, e.g., by changing the gene order, to allow expression of the enzymes in a desired level ratio such that the multi-enzyme complex exhibits a desired enzymatic specificity and enzymatic activity. The nucleotide sequence can further include a gene that encodes a scaffolding protein that is capable of binding to the enzymes. The nucleotide sequence can also include a gene encoding a microbial cell surface protein that is capable of binding to the scaffolding protein or is fused with the scaffolding protein. In some embodiments, the system can include a non-protein support, e.g., a polymer, a glass plate or bead, that is capable of binding to the enzymes.

The enzymes encoded by the nucleotide sequence can be any enzymes, e.g., cellulosomal enzymes, proteases, nucleases, lipases, laccases, amylases, or a mixture thereof. Each of the enzymes contains a ligand site (e.g., a dockerin domain) for binding to one of the receptor sites in the scaffolding protein or to a non-protein support. Cellulosomal enzymes refer to the catalytic proteins contained in a cellulosome, including, but are not limited to, cellulase, exoglucanase, endoglucanase (EG, β-1,4-endoglucanase, EC 3.2.1.4), cellubiohydrolase (EXG or CBHs, exo-β-1,4-glucanases, EC 3.2.1.91), β-glucosidase (BGLU, EC 3.2.1.21), xylanase, lichenase (β-1,3-1,4-endoglucanase), mannanase, chitinase, and endopygalactorunase. See Gold et al., J. Bacteriol. 189(19):6787-6795, 2007; Bayer et al., J. Structural Biol. 124:221-234, 1998; Demain et al., Microbiol Mol Biol Rev 69:124-154, 2005; and Wu, ACS Symp. Ser. 516:251-264, 1993. A cellulosomal enzyme can contain a Type-I dockerin domain for binding to a scaffolding protein containing a Type-I cohesin domain.

In one example, the nucleotide sequence encodes *C. thermocellum* CipA, CelS, CelK, CelA, XynC, and XynZ proteins. In another example, it further encodes *C. thermocellum* OlpB and CelR proteins. In yet another example, the nucleotide sequence encodes *C. thermocellum* CipA, CelS, CelK, CelA, CelR, sdbA, XynC, and XynZ proteins. As the positions of the multiple genes in the nucleotide sequence determine their expression levels, switching gene positions can adjust the relative expression levels among these genes.

In a further aspect, this invention features a vector containing the above-described expression cassette or a host cell (e.g., a bacterial cell, a yeast cell, or a mammalian cell) containing the vector. The host cell can be a mesophilic bacterium, e.g., *B. subtilis* or *E. coli*, or a mesophilic yeast.

Also within the scope of this invention is a method of degrading a biomass (e.g., a cellulose-containing biomass) with the host cell described above, which produces a protein complex containing the above-described scaffolding protein, enzymes, and optionally cell surface anchoring protein.

The details of one or more embodiments of the invention are set forth in the description below. Other features or advantages of the present invention will be apparent from the following drawings and detailed description of an example, and also from the appended claims.

BRIEF DESCRIPTION OF THE DRAWINGS

The drawings are first described.

DETAILED DESCRIPTION OF THE INVENTION

The present invention includes an expression system for producing multi-enzyme complexes and related methods. For example, cellulosomes are protein complexes produced by microorganisms for hydrolyzing insoluble polysaccharides, such as celluloses. Typically, a cellulosome contains a cell surface anchoring protein, a scaffoldin protein, and multiple cellulosomal enzymes. The scaffoldin protein, serving as a skeleton of the cellulosome, contains (a) one dockerin domain for binding to a cohesin domain in the cell surface anchoring protein, and (b) multiple cohesin domains each for binding to the dockerin domain in one of the multiple enzymes. The cellulosome can be anchored on cell surfaces via the cell surface anchoring protein. See Gold et al., J. Bacteriol. 189(19):6787-6795; 2007 and Bayer et al., J. Structural Biol. 124:221-234; 1998.

Expression System

The expression system includes a nucleic acid molecule, e.g., an expression cassette, containing a promoter operatively linked to a nucleotide sequence, e.g., a polycistronic nucleotide sequence, including multiple genes encoding enzymes that are components of the multi-enzyme complex. The genes of the nucleotide sequence are regulated artificially to allow expression of the enzymes in a desired level ratio such that the multi-enzyme complex exhibits a desired enzymatic specificity and enzymatic activity. The nucleotide sequence can further include a gene that encodes a scaffolding protein that is capable of binding to the enzymes. The nucleotide sequence can also include a gene encoding a microbial cell surface protein that is capable of binding to the scaffolding protein or is fused with the scaffolding protein. In lieu of a gene that encodes a scaffolding protein, the system can include a non-protein support, e.g., glass plate or bead, that is capable of binding to the enzymes.

(1) Enzymes

Any enzyme, either naturally occurring or genetically engineered, can be used in making the multi-enzyme complex mentioned above. To be incorporated into the complex using a scaffold protein, the enzyme includes a ligand site for binding to the scaffolding protein. Many naturally-occurring enzymes, e.g., those from microbial extracellular complexes, contain such ligand sites. If necessary, a ligand site can be inserted into an enzyme of interest by conventional methods.

The types of enzymes chosen for making the multi-enzyme complex described herein depend on the purpose of the multi-enzyme complex. For example, the enzymes can include an exoglucanase, an endoglucanase, a cellubiohydrolase, a β-glucosidase, a xylanase, a lichenase, a mannanase, a chitinase, an endopygalactorunase, a proteases, a nucleases, a lipases, a laccases, an amylases, or a β-galactosidase.

When the multi-enzyme complex is a cellulosome useful in degrading a cellulose-containing biomass, multiple cellulosomal enzymes, as described in Gold et al., 2007, can be used. Such cellulosomal enzymes can be derived from various sources, such as cellulolytic clostridia, (e.g., *C. cellulovorans*, *C. cellulolyticum*, and *C. papyrosolvens*), *Tricho-derma longibrachiatum*, *Bacteroides cellulosolvens*, *Acetivibrio cellulolyticusas*, *Neocallimastix frontalis*, and *Piromyces* spp. 12. When the multi-enzyme complex is designed for degrading other biomasses, other digestive enzymes can be used.

In a preferred embodiment, enzymes from a thermophilic microorganism (e.g., *Clostridium thermocellum*) are used. As such enzymes are thermo-stable, multi-enzyme complex containing them can exhibit high enzymatic activity at elevated temperature.

(2) Scaffolding Protein

A scaffolding protein can be any protein that provides multiple binding sites for anchoring multiple enzymes in a complex. It can be a naturally-occurring scaffolding protein found in a microorganism, e.g., in extracellular protein complexes such as cellulosome, pilus, flagella, and fimbriae, or a protein engineered to bind the enzymes. It contains (1) a ligand site (e.g., a dockerin domain) for binding to the receptor site in a surface anchoring protein, and (2) multiple receptor sites (e.g., cohesin domains) for binding to the multiple enzymes, each of which contains a ligand site (e.g., a dockerin domain). In some embodiments, the scaffolding protein is a cellulosomal scaffolding protein containing a dockerin domain (e.g., a Type-II dockerin) for binding to a cohesin domain (e.g., a Type-II cohesin domain) in a cellulosomal cell surface anchoring domain, and multiple cohesin domains (e.g., Type-I cohesin domains) for binding to enzymes that contain dockerin domains (e.g., Type-I dockerin domains). Non-specific cohesion-dockerin interactions can be employed. A cellulosomal scaffolding protein typically also includes one or more carbohydrate-binding modules. Examples of suitable scaffolding protein include, but are not limited to, CipA protein (e.g., from *C. thermocellum*), CbpA protein (e.g., from *C. cellulovorans*), and CipC protein (e.g., from *C. cellulolyticum*).

A scaffolding protein can also be a genetically engineered protein or a variant of a naturally-occurring scaffolding protein. Compared to its wild-type counterpart, the variant includes either a heterologous ligand/receptor site(s) or an increased copy number of the receptor site.

A scaffolding protein including a high number of receptor sites (e.g., up to 18) are preferred for preparing high order protein complexes, i.e., containing large numbers of enzyme molecules. Multiple scaffold proteins can also be linked together to create larger protein complexes.

(3) Support

A support can be any non-protein substrate, e.g., a polymer, a glass plate, a gold bead, and a nanoparticle, capable of binding to proteins. The enzymes described above can be immobilized on such support, in lieu of a scaffolding protein, to form a multi-enzyme complex. Methods for immobilizing proteins on a support are known in the art. For example, proteins can be immobilized on a support via nonspecific adsorption of the proteins to the support. Linkage of reactive groups (e.g., amine groups) within the proteins to complementary reactive groups (e.g., N-hydroxylsuccinimide groups) on a support surface can also be employed. Recombinant enzymes containing affinity tags (e.g., his tags) can be immobilized on a support by binding to functional groups (e.g., Ni-NTA) on the support.

(4) Microbial Cell Surface Anchoring Protein

A microbial cell surface anchoring protein, located on cell surfaces, contains a transmembrane domain and an extracellular domain. It can be a naturally-occurring cell surface anchoring protein of a microbial extracellular protein complex. Typically, such a surface protein contains a transmembrane domain and at least one receptor site (e.g., a cohesin domain) for binding to a scaffolding protein that contains a cognate ligand site (e.g., a dockerin domain). Other microbial cell surface proteins, which do not contain a ligand site for binding to a scaffolding protein, also can be used in the protein complex mentioned above. In that case, the cell surface protein can form a fusion protein with a scaffolding protein so as to display the latter on cell surfaces. Examples of a suitable cell surface anchoring protein include, but are not limited to, OlpB protein, SdbA protein, Orf2p protein (e.g., from *C. thermocellum*), ompC protein (e.g., from *E. coli*), ice nucleation protein, and partial ice nucleation protein. See U.S. Pat. Nos. 6,274,345 and 6,071,725.

Alternatively, a microbial cell surface anchoring protein is a genetically engineered variant of a naturally-occurring surface protein that includes a heterologous receptor site or an increased copy number of its endogenous receptor site. For preparing high order protein complex, a surface protein containing a high number of receptor sites (e.g., up to 14) is preferred.

(5) Nucleic Acid Molecule

To construct the nucleic acid molecule mentioned above, DNA fragments encoding the desired proteins can be isolated from their natural sources or prepared by genetic engineering via conventional methods. When PCR is applied to amplify these fragments, high-fidelity polymerases (e.g., KOD, Pfu) are preferred to reduce the possibility of introducing mutations during PCR. The DNA fragments can be ligated downstream to a suitable promoter in a suitable order to form the nucleic acid molecule. In one example, the ligation process is performed following the ordered gene assembly methods described in Tsuge et al. J. Biocteriol 183:5453-5458, 2001 and Tsuge et al., Nucleic Acid Res. 31:e133, 2003. In another example, it can be performed by conventional recombinant technology.

A promoter is a nucleotide sequence containing elements that initiate the transcription of an operably linked nucleic acid sequence. At a minimum, a promoter contains an RNA polymerase binding site. It can further contain one or more enhancer elements which, by definition, enhances transcription, or one or more regulatory elements that control the on/off status of the promoter. Selection of a suitable promoter for constructing the nucleic acid molecule depends on the type of host cell to which the nucleic acid molecule will be introduced. When *E. coli* is used as the host cell, suitable promoters include, but are not limited to the β-lactamase and lactose promoter systems (see Chang et al., *Nature* 275:615-624, 1978), the SP6, T3, T5, and T7 RNA polymerase promoters (Studier et al., *Meth. Enzymol.* 185:60-89, 1990), the lambda promoter (Elvin et al., *Gene* 87:123-126, 1990), the trp promoter (Nichols and Yanofsky, *Meth. in Enzymology* 101:155-164, 1983), the tac and trc promoters (Russell et al., *Gene* 20:231-243, 1982), and pCold (see U.S. Pat. No. 6,479, 260). When *B. subtilis* is chosen as the host cell, exemplary promoters include Pr promoter, Spo1 promoter, Tac promoter, and Lad promoter. These promoters can also be used in other bacterial hosts such as *Escherichia coli, Clostridium, Mycoplasma, Lactococcus, Lactobacillus, Vibrio,* and *Cyanobacteria*. Promoters for use in yeast (e.g., *Saccharomyces*) or other fungi (e.g., *Kluyveromyces, Pichia, Aspergillus, Trichoderma,* and *Candida*) include Lac4 promoter, Adh4 promoter, GapDH promoter, Adh1 promoter, Pgk promoter, Aac promoter, Pho5 promoter and Gal7 promoter.

In a preferred embodiment, an inducible promoter is used in constructing the nucleic acid molecule. Such a promoter is active only under a particular condition, e.g., presence of a particular compound (e.g., IPTG or tetracycline) or at a particular temperature (e.g., 40° C. or above).

The order of the genes in the nucleic acid molecules can be designed such that the enzymes encoded by the genes are expressed in a particular ratio, e.g., more of one specific enzyme than another. Consequently, by changing the order of the genes, the level ratio of the encoded enzymes in the multi-enzyme complex can be optimized to achieve specific enzymatic activity or specificity.

Inclusion of the desired genes in the nucleic acid molecule and their positions as designed can be confirmed by conventional methods, such as gene-specific PCR or restriction enzyme mapping. The nucleic acid molecule is then introduced into a suitable host cell for production of a protein complex. When necessary, two or more of the nucleic acid molecules described herein can be delivered into a host cell for expression of multiple proteins. If the desired genes encode thermophilic enzymes, the host cell preferably is mesophilic. Positive clones can be identified by, e.g., antibiotic resistance selection, and confirmed by examining the levels of the expected enzymatic activities. They can then be cultured under suitable conditions allowing expression of the proteins encoded by the genes and assembly of the protein complex.

Multi-Enzyme Complexes

The protein complex, either secreted, anchored on cell surfaces or a support, prepared as described above, can be used for various purposes, e.g., for degrading biomass and/or producing biofuels, depending upon the enzymes contained in the complex.

The multi-protein enzyme complexes can first be purified or isolated, e.g., from cell culture supernatant, before being employed for various purposes. For example, cellulosomes can be purified from cell culture supernatant using cellulose pellets. Alternatively, cells with multi-enzyme complexes anchored on the cell surface can be used directly to degrade biomass.

In a multi-enzyme complex, the enzymes, when at an optimal level ratio, act in synergism, thereby exerting high enzymatic activities. As mentioned above, switching the positions of the genes in the nucleic acid molecule changes their relative expression levels and consequently, the level ratio of the encoded proteins in the protein complex.

Accordingly, also described herein is a screening method for identifying a multi-enzyme complex that exhibits high enzymatic activity. To practice this method, a library of nucleic acid molecules described above, including nucleotide sequences encoding the same proteins but in different orders, can be constructed. The library can be introduced into suitable host cells. The transformed host cells that exhibit high enzymatic activities can be identified by, e.g., the methods described in the Example below. The nucleic acid molecules in these identified host cells can be characterized to determine their gene orders. These nucleic acid molecules, when introduced into suitable host cells, can produce multi-enzyme complexes with optimal protein level ratios to achieve synergistic effects among the enzymes.

Without further elaboration, it is believed that one skilled in the art can, based on the above description, utilize the present invention to its fullest extent. The following specific example is, therefore, to be construed as merely illustrative, and not limitative of the remainder of the disclosure in any way whatsoever. All publications cited herein are incorporated by reference.

EXAMPLE 1

Preparation and Characterization of *B. subtilis* Host Cells Expressing High-Order Cellulosomes DNA fragments encoding *Clostridium thermocellum* ATCC 27405 scaffolding protein CipA and cellulosomal enzymes exo-glucosidases CelK and CelS, endo-glucanase CelA, and xylanases XynC and XynZ were amplified by PCR using the KOD-Plus kit provided by TOYOBO CO., LTD., Japan. Scaffolding protein CipA contains one cellulose-binding module (CBM), one surface-layer homologous modules (SLH), and nine Type I cohesin domains.

The PCR products were cloned into plasmid pCR-XL-TOPO using the TOPO XL PCR Cloning Kit (Invitrogen, CA) and introduced into *E. coli* host cells following the method described in Mandel and Higa (Mandel and Higa, 1970). DNA plasmids were prepared from positive transformants using the Qiagen Plasmid Midi Kit (Qiagen, CA) and subjected to restriction enzyme digestion to produce fragments encoding the above listed cellulosomal proteins. After being extracted from agarose gels, the DNA fragments were used in gene assemble ligation.

An *E. coli/B. subtilis* shuttle vector pGETS118, described in Tsuge et al., Nucleic Acids Research 31:e133 (2003), was used for cloning the DNA fragments mentioned above. The copy number of this vector in *B. subtilis* is low and can be increased by 1 mM isopropyl 1-thio-b-D-galactoside (IPTG). The vector includes Pr promoter, which is thermo-inducible.

The DNA fragments encoding cellulosomal proteins were ligated into shuttle vector pGETS118 with the order CipA-CelS-CelK-CelA-XynC-XynZ using the ordered gene assembly in *Bacillus subtilis* using the method described in Tsuge et al., J. Bacteriol 183:5453-5458 (2003). More specifically, the DNA fragments (equal molar) were mixed with the vector, and the ligation reaction was carried out at 16° C. for 30 min using Takara ligation kit Ver. 1 in a 2-fold concentrated buffer [132 mM Tris±HCl (pH 7.6), 13.2 mM $MgCl_2$, 20 mM dithiothreitol, 0.2 mM ATP, 300 mM NaCl, 20% (w/v) polyethylene glycol 6000; Wako pure chemical, Japan]. High molecular weight linear DNA fragments were generated in this ligation reaction.

The linear DNA fragments mentioned above were introduced into a restriction-modification deficient mutant strain *B. subtilis* RM125 and into *B. subtilis* BUSY9166 described in Tsuge et al., 2003 as follows. Competent *B. subtilis* cells were prepared using the two-step culture method described in Anagnostopoulos and Spizizen, *J. Bacteriol.* 1961 81(5):741-6 (1961). A suitable amount of the linear DNA was mixed with 100 ml competent *B. subtilis* cells (in TFII) and incubated at 37° C. for 30 min. 300 ml LB was added to the DNA/cell mixture and the cells were cultured at 37° C. for 1 hour to allow expression of the tetracycline resistance gene carried by the cells. Afterwards, the cultured cells were spread on LB plates containing blasticidin S (500 mg/ml), chloramphenicol (5 mg/ml), erythromycin (5 mg/ml), neomycin (3 mg/ml), spectinomycin (50 mg/ml), and tetracycline (10 mg/ml) for selection of positive transformants.

Clones resistant to tetracycline at 30° C. were further analyzed by enzymatic analysis as follows. Each tetracycline-resistant clone was cultured in a medium (50 ml) containing 1 mM isopropyl 1-thio-b-D-galactoside (IPTG) for 5 hours at 30° C. and then shifted to 42° C. for 3 hours. The supernatant was then collected and concentrated by filtration using an Amicon filter (30 kDa cutoff). The level of UV-irradiated fluorescence in the filtrate was measured to determine the glucanase activity of the clone.

Two clones, Clone 1 and Clone 13, were identified as exhibiting glucanase activity in this study. Gene specific PCR analysis showed that each of the six cellulosomal genes mentioned above was amplified from DNAs prepared from the two clones by gene-specific primers. Restriction enzyme digestion analysis indicated that, in these two clones, the six genes were in the designed order.

(i) Examination of Enzymatic Activity pGETS-clone1, and pGETS-clone13, as well as *B. subtilis* containing empty vector pGETS (control clone), were grown at 30° C. in the LB medium supplemented with 12.5 ug/ml tetracycline for 6 hours. The cells were then incubated at 42° C. for 5 hours to induce expression of the cellulosomal proteins. Afterwards, the cell cultures were centrifuged at 5000 g for 10 mins. The supernatants were collected and concentrated against an exchange buffer (50 mM Tris, 10 mM $CaCl_2$ and 5 mM DTT pH6.8) using Viva Flow 50 (10 kDa cut off) (Sartorius, Goettingen, Germany) at 4° C. The cell pellets were also collected, resuspended in PBS, lysed by sonication (impulse: 3 secs; stop: 2 secs for 12 mins), and then centrifuged at 13200 rpm for 40 mins to remove pellets, resulting in samples containing intracellular proteins ("intracellular samples"). Alternatively, the cell pellets were collected and resuspended in PBS to produce samples containing intact cells.

The protein contents of the supernatants and intracellular samples were determined by the Bradford method. Both samples were subjected to enzymatic activity analysis as follows.

Figure 1:
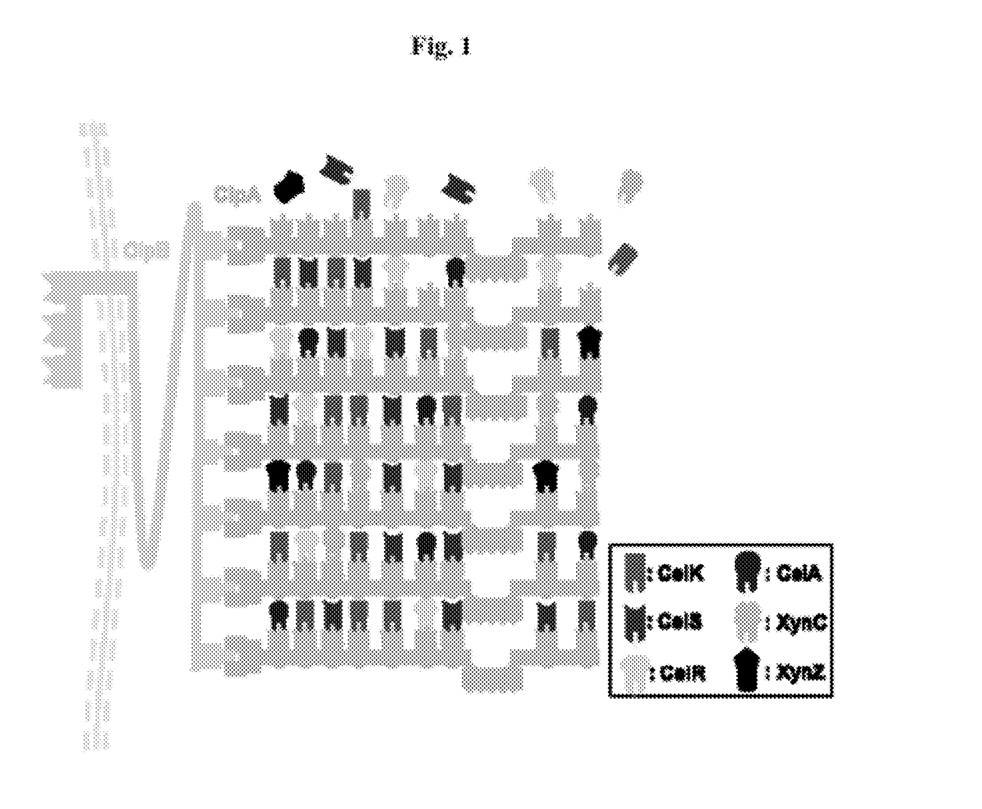
FIG. 1 is a schematic illustration depicting an artificial cellulosome anchored on a cell surface.
Figure 2:
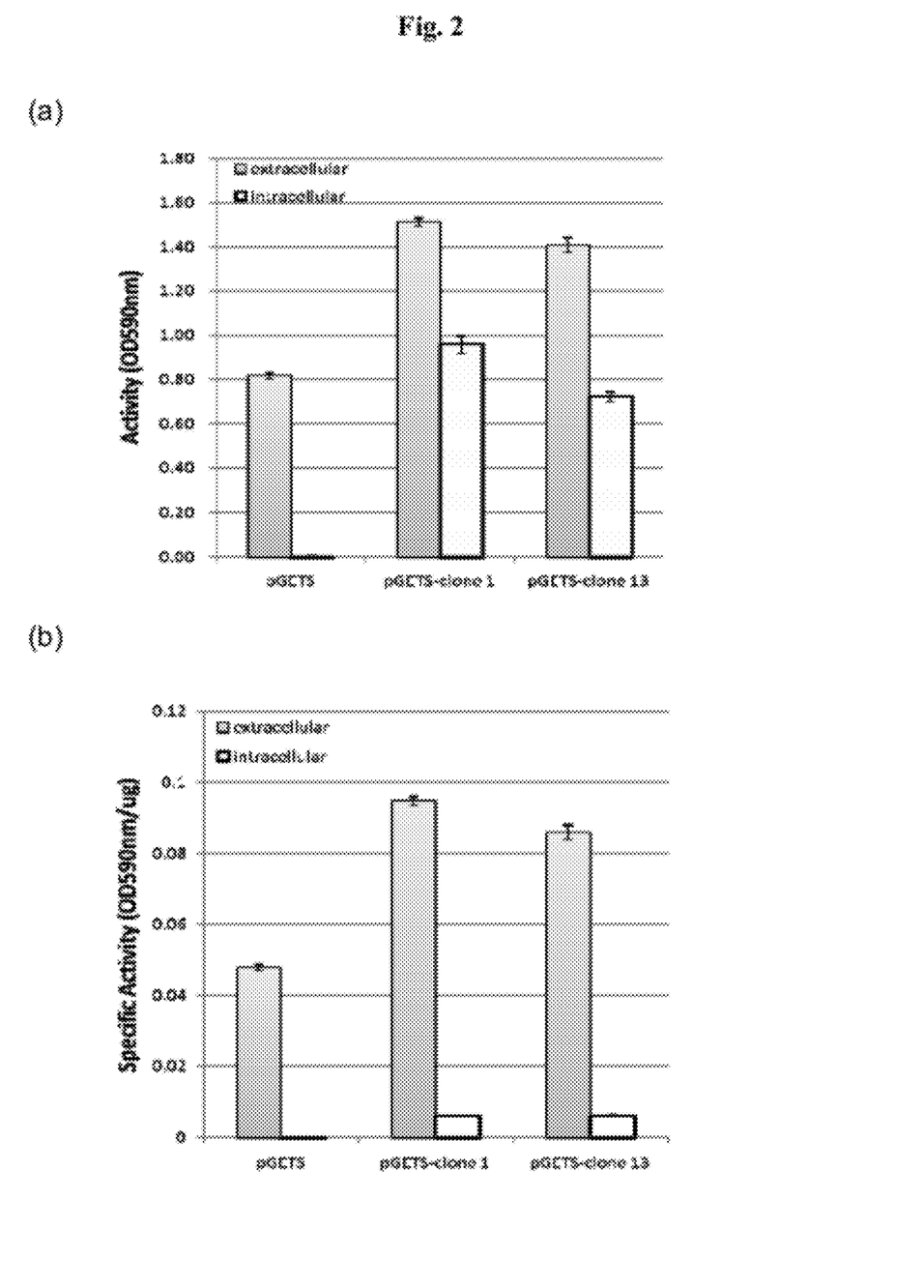
FIG. 2 is a chart showing extracellular and intracellular cellulolytic activity in *B. subtilis* host cells producing a protein complex containing *C. thermocellum* CipA, CelS, CelK, CelA, XynC, and XynZ proteins. (a): endo-glucanase activity determined with Azurin-linked β-glucan (dye CMC) as a substrate; (b) specific endo-glucanase activity, determined by normalizing endo-glucanase activity in a sample against its protein content; (c): total glucanase activity determined with 4-methylumbelliferyl-β-d-cellobioside (MUC) as a substrate; and (d): specific total glucanase activity, which is determined by normalizing total glucanase activity in a sample against its protein content.

Endo-glucanase activity was determined using Azurine cross-linked (AZCL)-β-glucan (dye CMC) (purchased from Megazyme) as the substrate. The supernatant and intracellular samples mentioned above were incubated with 1% (v/w) dye CMC in 50 mM sodium acetate (pH5.0) at 60° C. for 3 hours. The absorbance at 590 nm of each sample was then measured. The $OD_{590}$ values correlate with glucanase activity levels. The results indicate that the endo-glucanase activity in the supernatants of Clones 1 and 13 were 2 fold higher than that in the supernatant of the control clone. See FIG. 2(*a*). On the other hand, significant levels of the endo-glucanase activity were detected in the intracellular samples from Clones 1 and 13, while the endo-glucanase activity was not detectable in the intracellular sample from the control clone. See FIG. 2(*a*). Relative to the intracellular protein content of the control clone, those of Clones 1 and 13 were found to be significantly elevated, indicating that a certain amount of the exogenous proteins remained inside the cells as determined by the values of specific activity (enzymatic activity normalized against total protein content). See FIG. 2(*b*).

To examine the total glucanase activity, both supernatants and intracellular samples were mixed with 4-methylumbelliferyl-β-d-cellobioside (MUC) at a final concentration of 1 mg/ml in 50 mM sodium acetate buffer (pH 5.0) at 60° C. for 3 hours. The enzymatic activity was determined by fluorometry under UV irradiation at 365 nm in 1% $Na_2CO_3$. The results thus obtained show that the glucanase activities observed in the supernatants from Clones 1 and 13 were much higher than that observed in the supernatant from the control clone. See FIG. 2(*c*). Again, a certain amount of the exogenous proteins was found to be retained inside the cells. See FIG. 2(*d*).

(ii) Examination of Protein Complex Formation

The formation of cellulosomal protein complexes in Clones 1 and 13 was determined by SDS-PAGE. More specifically, extracellular protein samples prepared from the two clones (with no boiling) were subjected to electrophoresis on a 5-15% (w/v) polyacrylamide gel containing 0.1% SDS. The polyacrylamide gel was then placed on top of an agarose gel containing Xylan or CMC, and bubbles between the two gels were removed. The two gels were wrapped with a plastic membrane and incubated at 40° C. for 3 hrs (if the agarose gel contains CMC) or at 60° C. overnight (if the agarose gel contains Xylan). Afterwards, the polyacrylamide gel was separated from the agarose gel, fixed, and subjected to sypro ruby staining The agarose gel was immersed in 1 mg/ml Congo red for 30-60 mins and then in 1M NaCl for 10-60 mins. The position on the agarose gel where substrate CMC or Xylan was degraded appear as yellow and positions where no degradation occurs appear as dark-red. The polyacrylamide gel was also incubated in a solution (pH5.0) containing 0.2 mg/ml MUC and 50 mM NaOAc at 60° C. and 30 mins to detect its glucanase activity. Degradation of MUC was detected by examining the fluorescence level on the gel at 365 nm.

The results obtained from the above studies showed that both Clones 1 and 13 exhibited extracellular glucanase, xylanase, and β-glucosidase activity.

Proteins on the polyacrylamide gel mentioned above were transferred to a polyvinylidene difluoride membrane (GE) following the method described in Matsudaira, J. Biol. Chem. 262:10035-10038 (1987) or Salinovich and Montelaro, Anal. Biochem. 156:341-347 (1986). The membrane was blocked with PBS containing 5% skim milk, washed, and then incubated with an anti-rCipA antibody (1:5000 dilution) for 16 h at 4° C. After being washed for several times, the membrane was incubated with a HRP-conjugated goat anti-rabbit IgG (1:5000 dilution). After washing with PBS (pH 7.4), the membrane was incubated with a solution containing NBT/BCIP for signal development. The result indicated that the position of CipA protein in the polyacrylamide gel overlapped with the position where cellulase activity was observed.

Proteins at the position where cellulase activity was observed were extracted from the gel and subjected to protein mass analysis by a 5-15% (w/v) polyacrylamide gel and a two-dimensional DIGE gel electrophoresis. Peptides highly homologous to fragments of CelA, CelK, Cel S, CipA, and XynZ proteins were found in this analysis, indicating that these proteins form a protein complex and exhibits the expected enzymatic activity.

(iii) Examination of Enzyme Thermo-Stability

Figure 3:
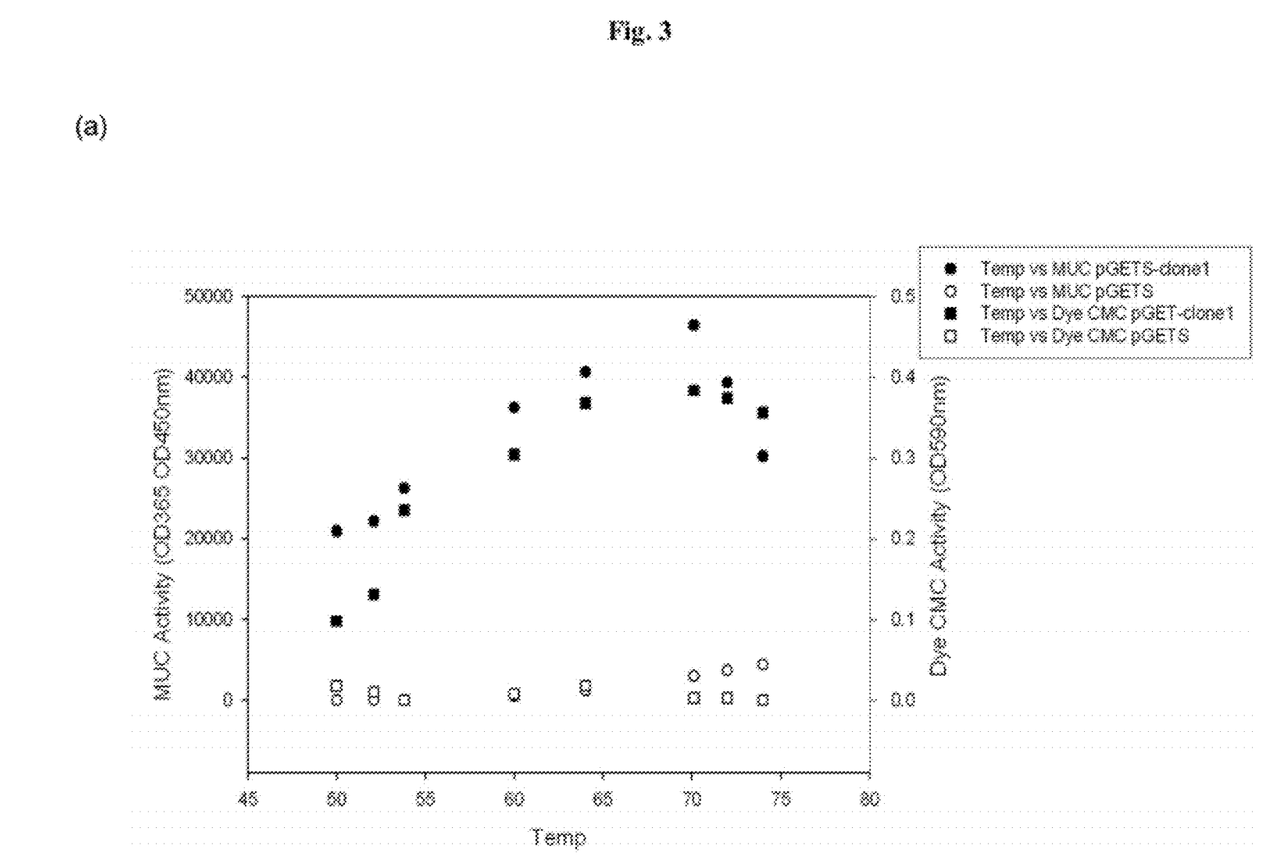
FIG. 3 is a diagram showing thermo-stability of cellulosomal glucanase in a protein complex, produced in *B. subtilis*, that contains *C. thermocellum* CipA, CelS, CelK, CelA, XynC, and XynZ proteins. (a): Glucanase activities of a control *B. subtilis* clone and two *B. subtilis* clones producing the protein complex under different temperatures; and (b): Glucanase activities and protein contents of a control *B. subtilis* clone and two *B. subtilis* clones producing the protein complex under different temperatures.

The extracellular cellulolytic activity of Clones 1 and 13 and the control clone was determined at different temperatures following the methods described above. Compared to the control clone, Clones 1 and 13 showed much higher enzymatic activity at temperatures above 50° C. and the differences were greater at higher temperatures. See FIG. 3(a). The extracellular protein contents of all three clones were found to be similar at each testing temperature. See FIG. 3(b). This indicates that the elevated enzymatic activity is due to thermo-stability of the cellulosomal enzymes expressed in Clones 1 and 13.

EXAMPLE 2

Figure 4:
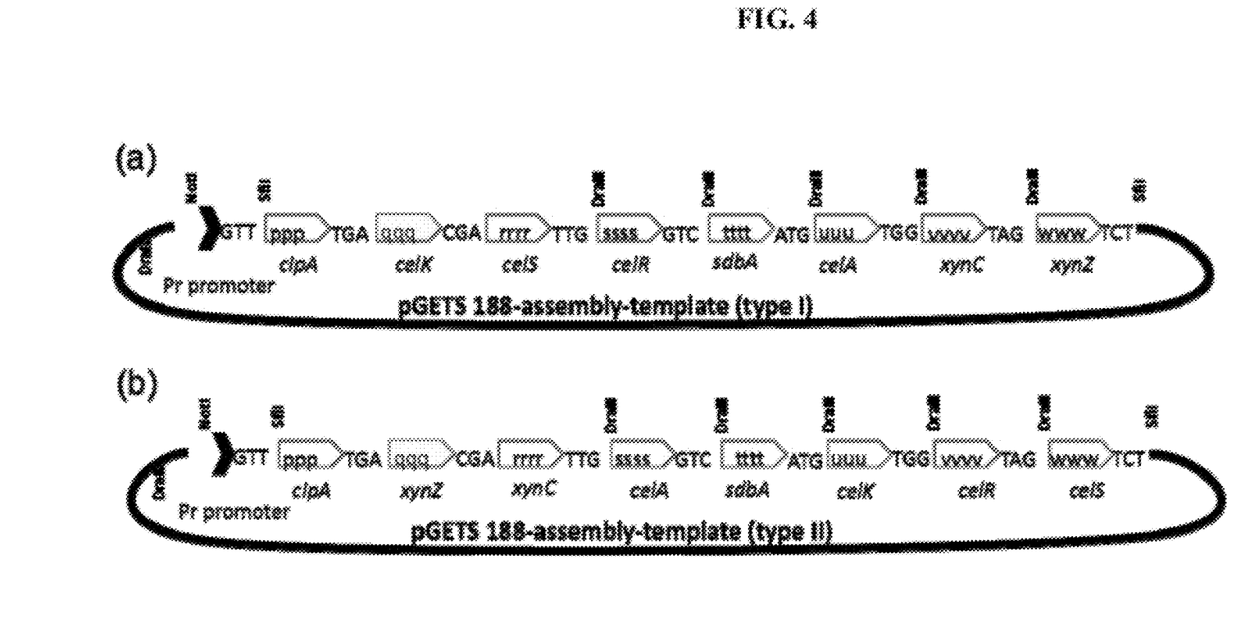
FIG. 4 is a schematic illustration of two plasmids containing cellulosomal genes: (a) Type I; (b) Type II

Preparation and Characterization of B. subtilis Host Cells Expressing Two Types of High-Order Cellulosomes In this study, two types of designed operon with genes in specific orders were constructed in B. subtilis using the methods described in Example 1 to express C. thermocellum "designer cellulosomes": Type I: cipA-celK-celS-celR-sdbA-celA-xynC-xynZ; and Type II: cipA-xynZ-xynC-celA-sdbA-celK-celR-celS. See FIG. 4(a) and FIG. 4(b). More specifically, the eight cellulosomal gene fragments were ligated into the pGETS 188 vector in designated orders and transform into B. subtilis by the OGAB method. Pr promoter was used as the sole promoter to drive the expression of the genes. A specific CI repressor mutant B. subtilis strain, BUSY 9797, was employed to improve the success rate of plasmid construction. Construction of the two desired plasmids was confirmed by Eco RI restriction enzyme digestion assay. Correctly-constructed plasmids, as well as empty pGETS 188 vector (control), were re-introduced into B. subtilis strain RM 125 for further assays.

Figure 5:
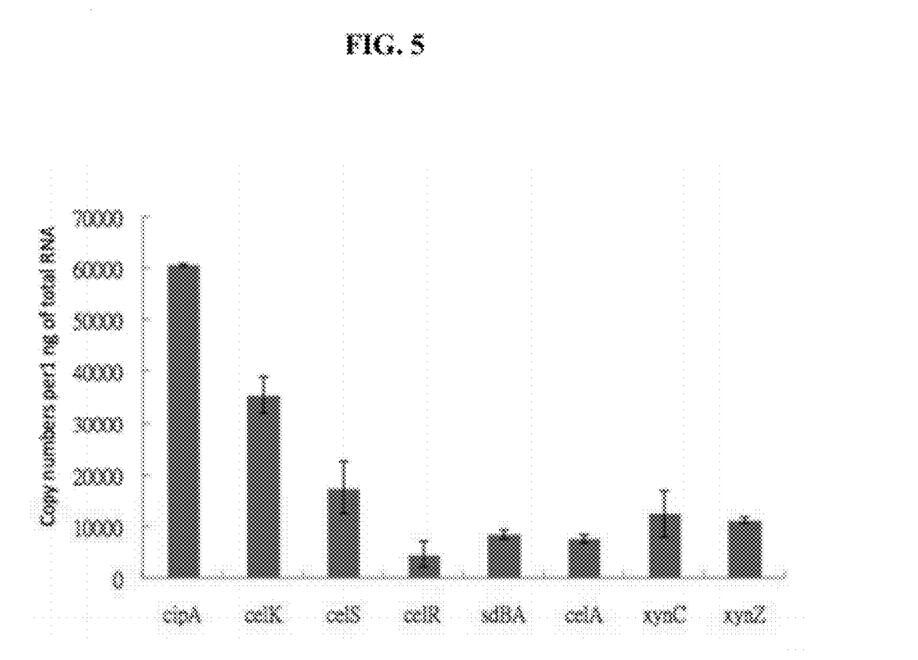
FIG. 5 is a bar graph showing expression level of the genes in Type I construct.

B. subtilis transformants containing expression plasmids were grown at 42° C. in liquid culture for 16 hours to induce expression of the cellulosomal genes. To confirm expression, total RNA was isolated from the cells for gene transcription assay. More specifically, template mRNA was purified from the cells using an RNeasy Protect Bacteria mini kit (High Pure RNA Isolation Kit, Roche). RT-PCR was performed with a reverse transcription kit (iScript cDNA synthesis kit, BioRad), the SYBR green I RT-PCR kit (Roche 480 SYBR green I master, Roche), and 8 gene-specific primer sets (the amplicon size was 113 to 137 bp) on a LightCycler (LightCycler 480, Roche). The standard template plasmid was prepared and quantitatively determine by spectrometer with 485 nm Ex/525 nm Em (SpectraMax M2) with SYBR green staining RT-PCR results indicated that all eight genes on Type I operon were transcribed under the control of the single Pr promoter. See FIG. 5. The data also suggest that the position of a gene in the operon modulates its expression level.

To determine whether the cellulosomal genes from C. thermocellum could be translated, and the resulting proteins secreted and assembled as cellulosomes in the heterologuse host of B. subtilis, the cellulosomal complexes, which possess the cellulose binding motif (CBM), were purified from the culturing supernatants for analysis. The B. subtilis transformants were cultured for 20 hrs, and 500 ml of each culture was centrifuged at 8,000 g for 60 min at 4° C. 300 ml of supernatant was mixed with 2 g of Avicel-cellulose. The mixture was adjusted to 50 mM phosphate buffer (pH 7) to a final volume of 4 ml. After 1 hr of incubation at 4° C., cellulose pellets were collected by centrifugation and washed twice with phosphate buffer. Proteins adsorbed onto the cellulose pellets were eluted by boiling the pellets for 10 min in 100 ml of SDS-PAGE loading buffer. The eluted proteins were subjected to SDS-PAGE analysis. After SDS-PAGE electrophoresis, some distinguishing bands (band 1, 3, 4, 5, 6, and 7) appeared in the Type I and Type II samples and the molecular weights of these bands were determined to be those of CipA (192.8 kD), CelK (100.6 kD), XynZ (92.2 kD), CelS (83.5 kD), CelR (82 kD), XynC (69.5 kD), and CelA (52.5 kD). See FIG. 6 (a). Some proteins (band 2, 8, 9, 10, and 11) at molecular weights about 125, 40, 35, 20, and 15 kD were identified as the partial fragments of CipA by protein mass spectrometry. These data demonstrated that all of the cellulosomal proteins were assembled on the scaffoldin protein CipA, and the CBM retained its cellulose adsorption ability.

Figure 6:
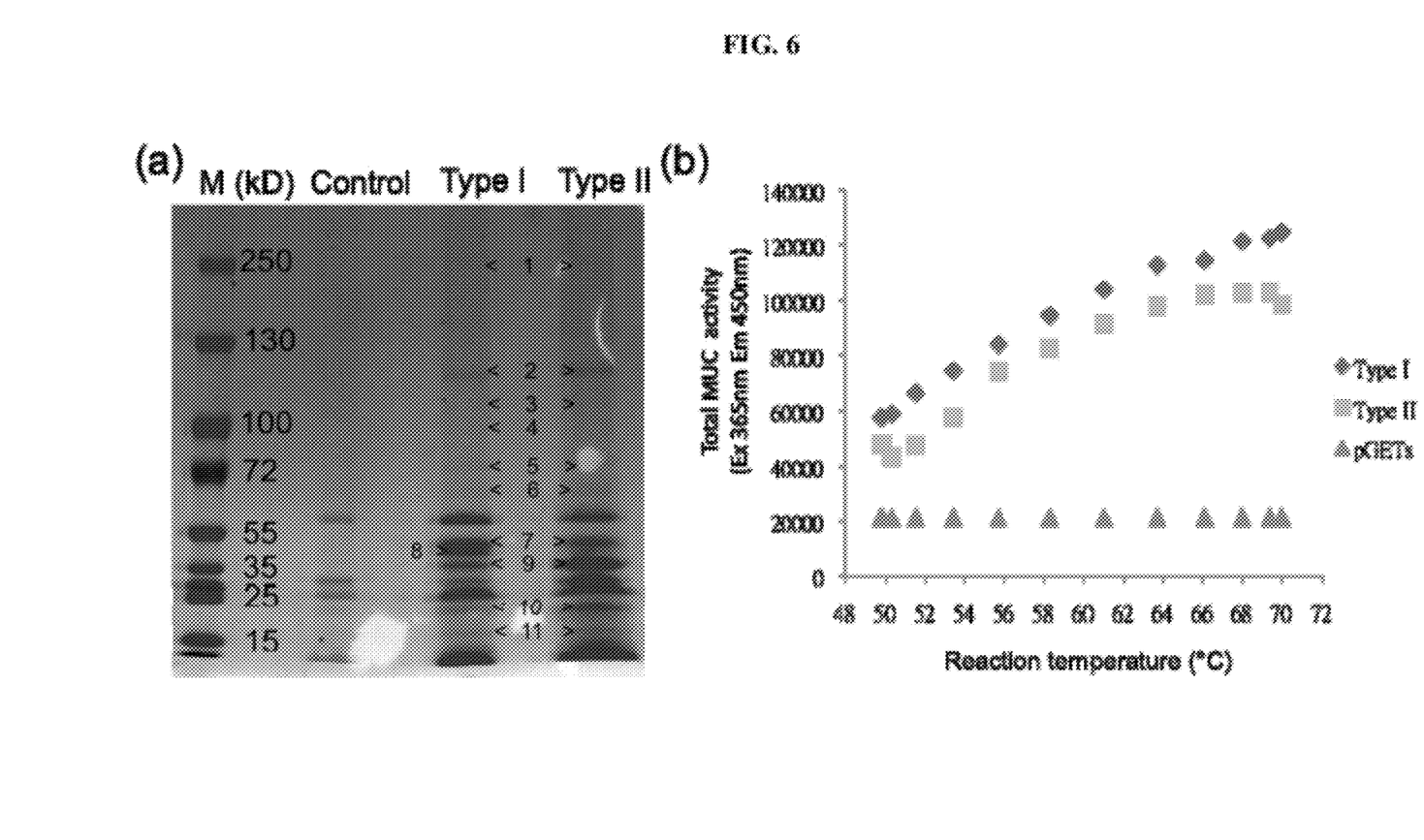
FIG. 6 is a diagram showing that using Type I and Type II constructs, (a) cellulosomal proteins were expressed and bound to the scaffold protein by SDS-PAGE and (b) the cellulosome was thermo-stable using a MUC assay of total glucanase activity.

In previous studies, native cellulosomes expressed in the thermophilic bacterium, C. thermocellum were shown to displayed maximum activity at 70° C. (see, e.g., Kruus et al., J. Bacteriol. 1995 March; 177(6):1641-1644; and Johnson et al., 1982 Appl Environ Microbiol 43(5):1125-1132). MUC assays performed at different temperatures to determined total glucanase activities of the purified cellusomal proteins showed that the Type I and Type II cellusomes expressed in B. subtilis remained as thermo-stable as native cellulosomes. See FIG. 6(b).

Figure 7:
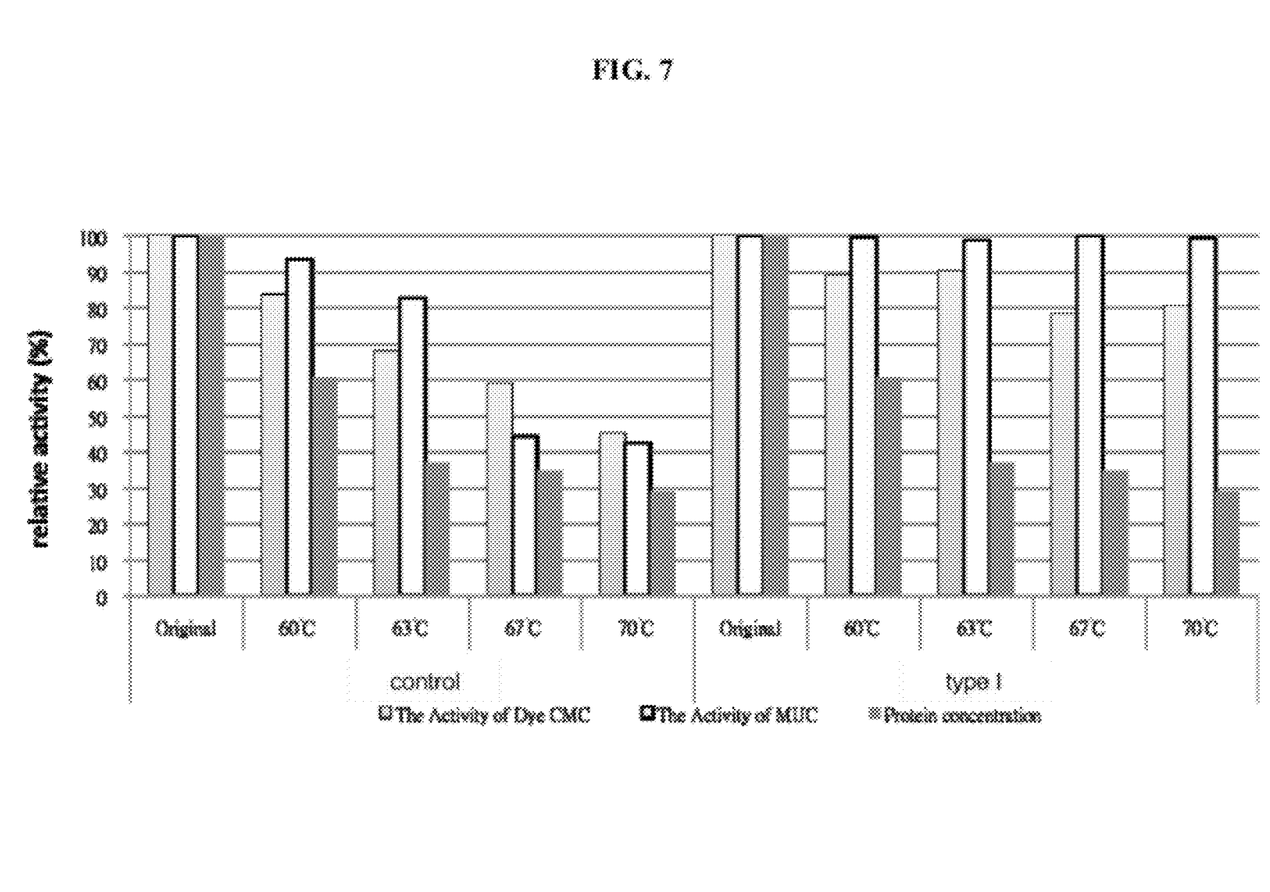
FIG. 7 is a bar graph showing the glucanase activity and total protein concentration at various temperatures of Type I cellulosomes expressed in *B. subtilis*.

To verify the cellulosomal functions of the B. subtilis clones, samples from the cell culture supernatants were condensed 10 folds with $CaCl_2$-containing and low DTT-concentration buffer, and prepared without boiling for cellulosomal protein definition. The thermo-stability of the proteins in the supernatants was also tested by heating at different temperatures for 30 minutes. The denatured and non-thermo-stable proteins were removed from solution. The amount of the proteins remaining and their enzymatic activities were determined. Although the heating treatment caused degradation of more than 50% of the secreted proteins in both the Type-I and vector-only clones, the Type I-clone retained 8% more proteins than the vector-only control at 70° C. treatment. See FIG. 7. The weaker native endo-glucanase activity in the control clone was destroyed at higher temperatures. See FIG. 7. On the other hand, using MUC and CMC as substrates, it was shown that 80-95% of the glucanase activity of Type I-clone remained after heat treatments. See FIG. 7.

The formation of cellulosomal protein complexes in clones Type I and Type II was determined by SDS-PAGE and zymogram as described in Example 1. The results revealed that the secreted proteins of the two clones showed apparent specific glucanase activity on the MUC, xylane, and CMC zymograms as compared to the vector-only control. There was one smear area that showed multi-glucanases activity with MUC, xylane, and CMC as substrates on the zymograms. The spots in the area were identified as CelK, XynZ, CelS, CelR, XynC, and CelA by mass spectrometry. These data demonstrated that cellulosome subunits with glucanase activity could interact and assemble on the scaffold protein CipA.

For quantitative enzymatic activity analysis, both the supernatant and intracellular samples from the three *Bacillus* clones (Type I, Type II, and vector-only control) cultures were harvested. The transformants were grown at 30° C. in LB medium supplemented with 12.5 ug/ml of tetracycline. After 6 hrs the cells were induced at 42° C. and then 5 hrs later the supernatants were harvested by centrifuging at 5000 g for 10 mins. The supernatants were then condensed 100× and the buffer (50 mM Tris, 10 mM $CaCl_2$ and 5 mM DTT pH6.8) was exchanged by Viva Flow 50 (10 kDa cut off) (Sartorius, Goettingen, Germany) at 4° C. The cells were collected, resuspended in PBS, lysed by sonication (impulse: 3 secs; stop: 2 secs for 12 mins), and then centrifuged at 13200 rpm for 40 mins to remove pellets, resulting in samples containing intracellular proteins.

Figure 8:
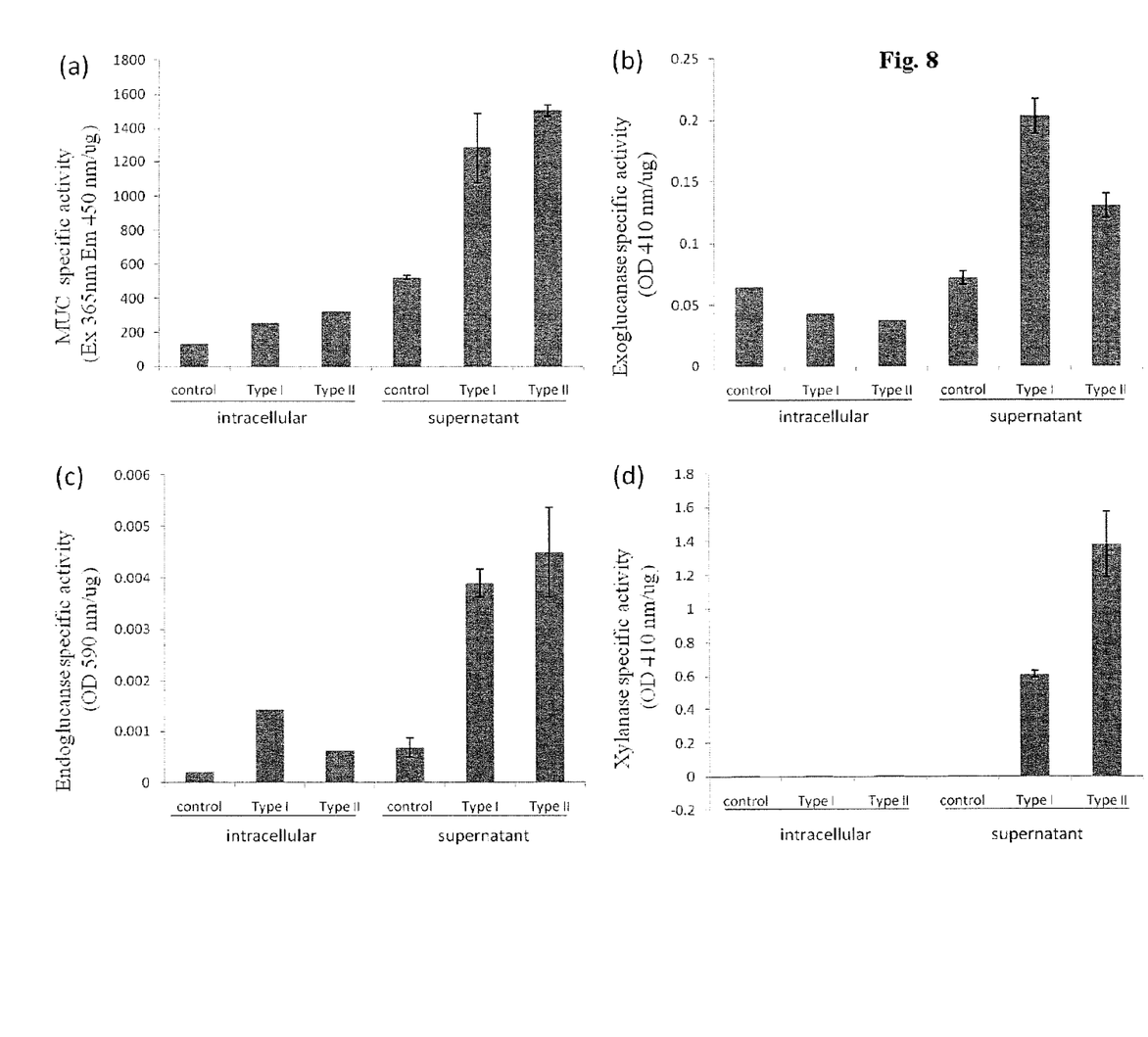
FIG. 8 is a set of bar graphs showing the cellulytic specificity and activity of Type I and Type II cellulosomes: (a) total activity assay by MUC assay; (b) exoglucanse activity by avicel assay; (c) endoglucanase activity by dye CMC assay; (d) xylanase activity by xylane substract.

MUC was used as the substrate to determine cellulosomal cellulolytic activity, and the results indicated that the total glucanase activities in the supernatants of both Type I and Type II clones were considerably higher than that of the control clone. See FIG. 8(a). A low level of enzymatic activity due to incomplete protein secretion could be detected in the intracellular sample. See FIG. 8(a). Data also showed that the exo-glucanase activities in the supernatants of both clones were high, the activity of Type I clone being higher than that of the Type II clone. See FIG. 8(b). Assays performed with dye CMC as a substrate demonstrated that the endo-glucanase activities in the supernatants of the two clones were about the same. See FIG. 8(c). Further, assays performed with xylane as a substrate showed that the total xylanase activity in the supernatant of the Type II clone was the highest among all samples examined. See FIG. 8(d). The differences in the cellulosomal cellulolytic activities of the Type I and Type II clones may be attributed to enzyme synergism and the different orders of the genes in the two expression vectors.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An expression system for producing a multi-enzyme complex, the system comprising a nucleic acid molecule containing a promoter operatively linked to a nucleotide sequence including *C. thermocellum* genes encoding proteins that are components of the multi-enzyme complex, wherein the promoter is the lambda Pr promoter, the *C. thermocellum* genes include cipA, celK, celS, celR, sdbA, celA, xynC, and xynZ, and the genes of the nucleotide sequence are regulated artificially to allow expression of the enzymes in a desired level ratio such that the multi-enzyme complex exhibits a desired enzymatic specificity and enzymatic activity.

2. The system of claim 1, wherein the genes are regulated artificially by positioning the genes within the nucleotide sequence in a specific order, by including an inducible promoter, by including more than one promoters, or by increasing the copy number of a gene.

3. The system of claim 1, wherein the multi-enzyme complex is a cellulosome.

4. The system of claim 1, wherein the order of the genes in the nucleotide sequence is cipA, celK, celS, celR, sdbA, celA, xynC, and xynZ, cipA being proximal to the promoter.

5. The system of claim 1, wherein the order of the genes in the nucleotide sequence is cipA, xynZ, xynC, celA, sdbA, celK, celR, and celS, cipA being proximal to the promoter.

6. A host cell for expressing a cellulosome, the host cell comprising a nucleic acid molecule containing a promoter operatively linked to a nucleotide sequence including *C. thermocellum* genes encoding proteins that are components of the cellulosome, wherein the promoter is the Pr promoter, the *C. thermocellum* genes include cipA, celK, celS, celR, sdbA, celA, xynC, and xynZ, and the genes of the nucleotide sequence are regulated artificially to allow expression of the enzymes in a desired level ratio such that the multi-enzyme complex exhibits a desired enzymatic specificity and enzymatic activity.

7. The host cell of claim 6, wherein the host cell is a *B. subtilis*, an *E. coli*, a *Lactobacillus*, an algal, or a yeast.

8. A method of producing a cellulosome, the method comprising
growing the host cell of claim 6 in a liquid culture under conditions that allow expression of the proteins that are components of the cellulosome, whereby the proteins assemble to form the cellulosome.

9. The method of claim 8, further comprising collecting a supernatant of the culture and isolating the cellulosome from the supernatant using cellulose pellets.

10. The method of claim 8, further comprising isolating the cells from the culture.

11. The host cell of claim 6, wherein the host cell includes a cellulosome anchored to the surface of the cell.

12. A method of degrading a biomass, the method comprising
providing the host cell of claim 11;
growing the host cell in a liquid culture under conditions allowing expression of the cellusome;
collecting (i) the cell or (ii) a supernatant of the culture and isolating the cellusome from the supernatant; and
contacting the collected cell or the isolated cellusome with a biomass, whereby the cellusome on the collected cell or the isolated cellusome degrades the biomass.

* * * * *